United States Patent
DelloStritto et al.

(10) Patent No.: US 8,688,187 B2
(45) Date of Patent: Apr. 1, 2014

(54) PULSE OXIMETER

(75) Inventors: James J. DelloStritto, Jordan, NY (US); Adam Paul Vallee, Cato, NY (US); Ajay Chandrakant Pawar, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 632 days.

(21) Appl. No.: 12/908,115

(22) Filed: Oct. 20, 2010

(65) Prior Publication Data

US 2012/0101349 A1   Apr. 26, 2012

(51) Int. Cl.
*A61B 5/1455*   (2006.01)

(52) U.S. Cl.
USPC .............................. 600/323; 600/344; 600/310

(58) Field of Classification Search
USPC .................................. 600/310, 322, 323, 344
See application file for complete search history.

(56) References Cited

U.S. PATENT DOCUMENTS

| | | | |
|---|---|---|---|
| 5,999,834 A | 12/1999 | Wang et al. | |
| 6,377,829 B1 | 4/2002 | Al-Ali | |
| 6,725,075 B2 | 4/2004 | Al-Ali | |
| 6,748,254 B2 * | 6/2004 | O'Neil et al. | 600/344 |
| 6,839,585 B2 | 1/2005 | Lowery et al. | |
| 6,920,345 B2 | 7/2005 | Al-Ali et al. | |
| 7,225,007 B2 | 5/2007 | Al-Ali et al. | |
| 7,486,977 B2 | 2/2009 | Sweitzer et al. | |
| 7,499,739 B2 * | 3/2009 | Sweitzer et al. | 600/323 |
| 7,736,310 B2 | 6/2010 | Taub | |
| 8,135,447 B2 * | 3/2012 | Kondoh et al. | 600/310 |
| 2005/0228299 A1 | 10/2005 | Banet | |
| 2007/0142715 A1 | 6/2007 | Banet et al. | |
| 2007/0244378 A1 | 10/2007 | Al-Ali et al. | |
| 2011/0060196 A1 * | 3/2011 | Stafford | 600/309 |

FOREIGN PATENT DOCUMENTS

WO   WO 2007/015833 A2   2/2007

OTHER PUBLICATIONS

Thomsen et al., Distributed Sensors: Applications, Fabrication and Challenges.
Dunn et al., A Novel Ring Shaped Photodiode for Reflectance Pulse Oximetry in Wireless Applications, IEEE Sensors 2007 Conference, 2007, pp. 596-599.
Netguard Technical Handbook, 2010, Mindray DS USA, Inc.
PureLight SpO2 Sensors Product Brochure, 2005, Nonin Medical, Inc.
Dresher, Wearable Forehead Pulse Oximetry: Minimization of Motion and Pressure Artifacts, A Thesis Submitted to the Faculty of the Worcester Polytechnic Institute, May 3, 2006.

(Continued)

*Primary Examiner* — Eric Winakur

(57) ABSTRACT

A pulse oximeter includes a housing defined by at least a first housing portion and a second housing portion wherein the second portion includes a passage. A sensor module disposed in the housing and proximate the passage includes at least one light emitting diode and at least one photodetector. A processing module also disposed in the housing and configured to communicate with the sensor module includes at least a processor, a network interface, and a power supply. The pulse oximeter further includes a pad having at least a bottom surface and a pad passage, as well as an adhesive configured to be disposed on at least a portion of the bottom surface of the pad. The housing is configured to releasably engage the pad wherein the housing passage and the pad passage are substantially aligned with one another.

19 Claims, 2 Drawing Sheets

(56) References Cited

OTHER PUBLICATIONS

Haahr et al., A Wearable "Electronic Patch" for Wireless Continuous Monitoring of Chronically Diseased Patients, IEEE, Proceedings of the 5th International Workshop on Wearable and Implantable Body Sensors, Sensor Network, in conjunction with the 5th International Summer School and Symposium on Medical Devices and Biosensors, The Chinese University of Hong Kong, HKSAR, China, Jun. 1-3, 2008, pp. 66-70.

* cited by examiner

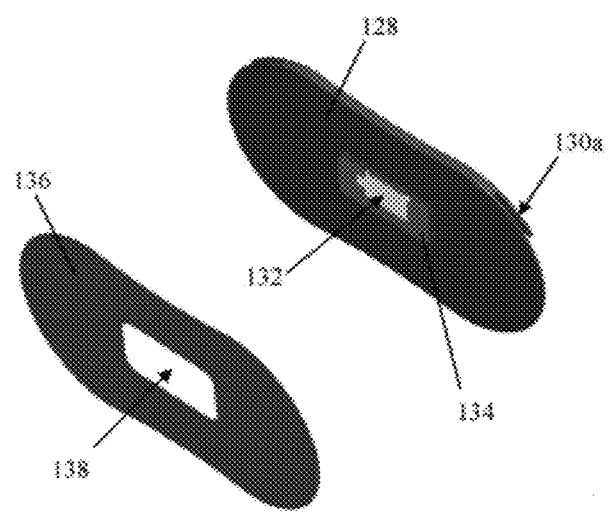
Fig. 2
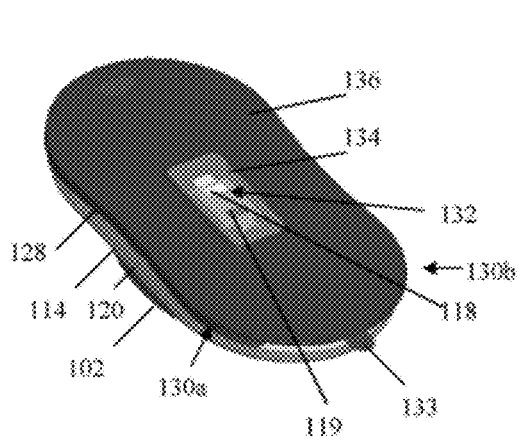
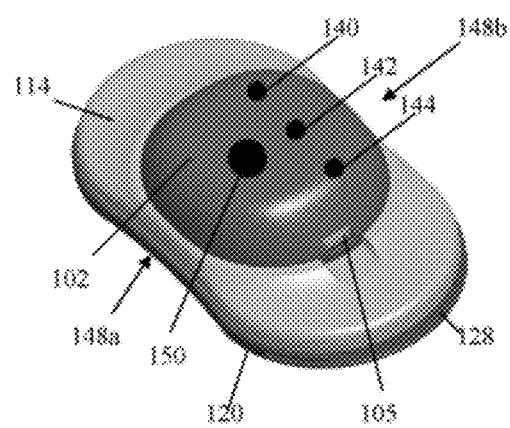
Fig. 3a                                 Fig. 3b

PULSE OXIMETER

TECHNICAL FIELD

The present invention generally relates to the field of diagnostic instruments including wearable sensors and more particularly to a disposable, wearable adhesive pad configured to engage a pulse oximeter sensor module disposed in a reusable housing.

BACKGROUND

Pulse oximeter assemblies include sensors that are configured to measure the oxygen saturation of the blood and are of particular importance in emergency medical situations as well as the monitoring of patients with respiratory or cardiac problems. Generally, pulse oximeters operate by directing light, such as in the red and/or infrared wavelength range, from one or more light emitting diodes (LEDs) toward the skin and blood vessels. According to one exemplary assembly, two LEDs are provided wherein one LED is configured to emit light in the red wavelength range and the other is configured to emit light in the infrared range. In operation, the pulse oximeter assembly emits light from both LEDs and a photodiode collects the light reflected from the patient's body. Because light in the red wavelength range is absorbed at a different rate than the infrared light, the ratio of oxyhemoglobin and deoxyhemoglobin can be calculated from the respective amounts of reflected light. To reduce potential interference, prior art pulse oximeter sensors are generally configured to be worn on intrusive portions of the body such as fingers or ear lobes.

Increasingly, pulse oximeter sensors are wearable and capable of continuous, wireless, and remote monitoring patients. In order to be less intrusive, pulse oximeters have been designed to be disposed on the forehead or chest region of the patient's body, among other location. However, prior art body-worn sensors are generally either single use or single patient use only or require a disinfecting process prior to subsequent use. Disposing of pulse oximeter sensors is costly and a waste of resources while disinfecting the sensors is also costly, a waste of resources, particularly in terms of collection and redistribution of sensors, and still susceptible to an increased risk of spreading contaminants such as bacteria and pathogens that could lead to the outbreak of disease.

Accordingly, there is a need for a wearable pulse oximeter sensor that is capable of reuse while not requiring disinfecting thereby providing for more convenient and less costly means for sensing blood parameters, as well as reduced risk of spreading disease.

BRIEF DESCRIPTION OF THE DRAWINGS

The present invention is disclosed with reference to the accompanying drawings, wherein:

FIG. 2 is a perspective view of an exemplary disposable pad and adhesive strip according to one embodiment of the present invention; and FIGS. 3(a) and 3(b) are bottom and top perspective views of an exemplary pulse oximeter according to one embodiment of the present invention.

Figure 1:
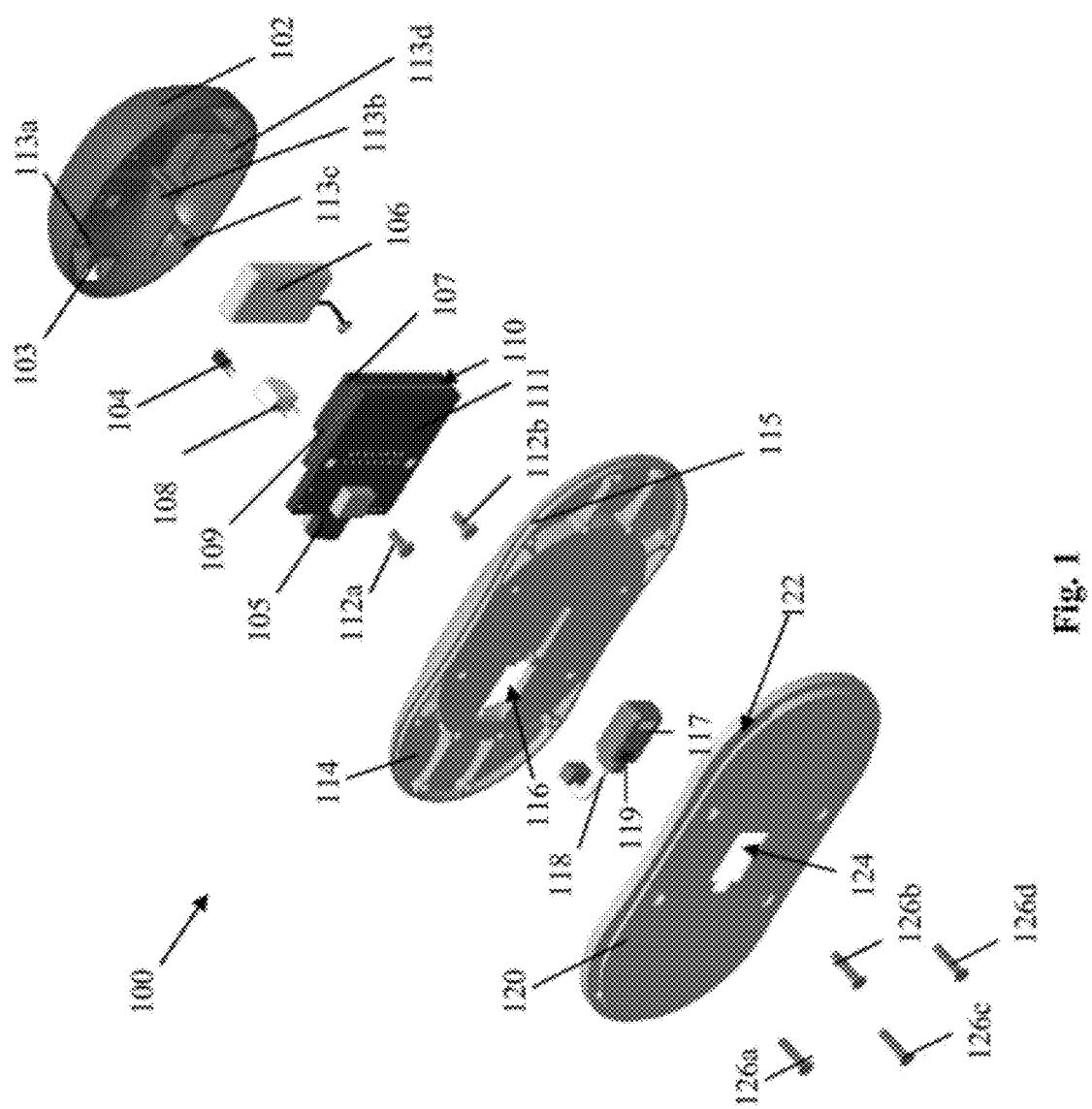
FIG. 1 is an exploded view of an exemplary pulse oximeter according to one embodiment of the present invention.

It will be appreciated that for purposes of clarity and where deemed appropriate, reference numerals have been repeated in the figures to indicate corresponding features.

DETAILED DESCRIPTION

Referring to FIG. 1, an exploded view of one exemplary embodiment of a pulse oximeter assembly 100 according to the present invention is shown as including a reusable housing including a top housing portion 102, a main housing portion 114, and a bottom housing portion 120 in which the main housing portion is disposed intermediately between the top housing portion 102 and the bottom housing portion 120. Although the housing portions 102, 114 and 120 are shown separately, any combination of housing portions 102, 114, and 120 can be connected, attached, combined or molded together, wherein the present version provides merely one example. In one embodiment, the top housing portion 102 is comprised of a durable material such as a polycarbonate acrylonitrile butadiene styrene polymer and each of the main and bottom housing portions 114, 120 are made up of a suitably flexible material, such as a thermoplastic polyurethane elastomer. Other suitable materials can be utilized. At least the bottom housing portion 120 includes at least one passage 124 configured to permit substantially unobstructed passage of light. Accordingly, the passage 124 can be an open aperture or a section of a substantially transparent thermoplastic, for example, fitted within the aperture. The housing, and more specifically the bottom housing portion 120 in the exemplary embodiment shown in FIG. 1, further includes at least one peripheral groove 122. In one preferred embodiment, opposing perimeter portions of the bottom housing portion 120 each include a groove portion 122 (only one being shown in FIG. 1). The housing portions 102, 114, and 120 can be assembled together by screws 126, such as flat head thread-forming screws, extending through apertures in housing portions 120 and 114 and received by a corresponding set of molded posts 113 that are formed within the interior of the top housing portion 102. In those embodiments including more than one housing portion, other means of engagement are contemplated such as by interlocking peripheral groove 115, adhesive, snap(s), flexible tab(s), latch(es), and/or clip(s), for example.

Disposed in one or more of the housing portions 102, 114 and 120 is a sensor module 118, which includes at least one light emitting diode (LED) 119 configured to emit light such as in the red and/or infrared range and at least one photodetector 117 configured to receive the light emitted by the at least one LED 119 and reflected by a patient's body (not shown) when in use and disposed proximate the body. One exemplary sensor module 118 is an 8000R Reflectance Sensor available from Nonin Medical Inc. According to the embodiment depicted, the sensor module 118 is adapted to be fitted within an opening formed in the main housing portion 114.

The sensor module 118 is configured to electrically communicate with a processing module 110, which is also configured to be disposed in relation to the main housing portion 114, for example, and proximate to the passage 124. The processing module 110 includes at least a processor 107, at least one network interface 105, a power supply 106 and optionally, data storage means 109. The network interface 105 can be configured to communicate data by a protocol such as universal serial bus (USB), Wi-Fi, Bluetooth, IrDA, radio frequency, IEEE 802.11, IEEE 802.15, and/or Zigbee. One exemplary power supply 106 is a 110 mAh, 3.7 v battery, though it will be readily apparent that any convenient portable power source can be employed. The data storage means 109 can include local, network-accessible, removable/nonremovable, volatile/nonvolatile, and/or transitory/nontransitory memory, such as RAM, ROM, firmware and/or flash and can be further configured to store program instruction that, when implemented by the processor, are configured to communicate with the sensor module 118 and specifically to operate the LED(s) 119 and photodetector 117 so as to receive data/information based on light reflected from the patient's body when the pulse oximeter is in use. One or more of the processor, network interface, power supply 106, and data storage means 109 can be configured to mount on a printed circuit board 111 of the processing module 110. The printed circuit board 111 is optionally attached by screws 112 such as pan head thread-forming screws extending through apertures in the printed circuit board 111 and received by the top housing portion 102. Other means of attachment, however, are contemplated such as adhesive, snap(s) and/or clip(s), for example. Optionally, a power button 108 is disposed in the housing portion and configured to communicate with the processing module 110 to engage the power supply 106 and disengage the power supply 106 upon user interaction with the switch 108. Also optional is a power status indicator LED 104 disposed so as to be visible externally through a formed aperture 103 in the top housing portion 102.

Referring to FIG. 2, a perspective view of an exemplary embodiment according to the present invention is shown as including a disposable pad 128 and an adhesive strip 136 wherein each includes at least one passage 132 and 138, respectively. Passage 138 of the adhesive strip 136 is configured to be substantially aligned with passage 132 of the pad 128 when the adhesive strip is disposed on the pad 128. The passages 132 and 138 are configured to permit substantially unobstructed passage of light such as emitted by the LED(s) 119 of the sensor module 118. Accordingly, the passages 132, 138 can be defined by an open aperture 138 or alternatively, one or more of the passages 132 and 138 can be defined by a section of a substantially transparent thermoplastic such as a translucent, clear, high-clarity virgin polypropylene 134, for example. The adhesive strip 136 can be formed of a medical grade adhesive separately applied to the pad 128, for example. The pad 128 can be comprised of a flexible material including polypropylene, pellethan, and/or a Lexan polycarbonate resin thermoplastic, for example and further includes at least one tongue 103 configured to releasably engage the bottom housing portion 120 at the at least one groove portion 122, such as by slidably receiving the bottom housing portion 120, so as to substantially align at least passages 124, 132 and 138 thereby providing substantially unobstructed access of the LED(s) 119 to the patient's body when the pulse oximeter 100 is in use. Other means of attachment of the bottom housing portion 120 relative to the pad 128 are contemplated and can include hook(s) and loop(s) fasteners, one or more snap(s), one or more magnet(s) and/or one or more clip(s).

In one exemplary embodiment, the sensor module 118 is attached to the disposable pad 128 at the pad passage 132 so as to directly access the patient's body (not shown) when the pulse oximeter 100 is in use. In this exemplary embodiment, the sensor module 118 is configured to electrically communicate with the processing module 110 upon engagement of the bottom housing portion 120 and the pad 128. The electrical communication can be facilitated by electrical contact(s) (not shown), optionally disposed on a surface of the bottom housing portion 120, and attached to the processing module 110, and/or by releasable engagement with the processing module 110 such as by plugging into the printed circuit board 111, accessible by the sensor module 118 through one or more of passages 124, 116 in the bottom and main housing portions 120, 114, respectively.

Referring to FIG. 3a, a bottom perspective view of an exemplary embodiment of a pulse oximeter according to the present invention is shown wherein the pad 128 is engaged with the bottom housing portion 120. Attached to the exterior surface of the pad 128 is an adhesive strip 136, including an optional tab 133 for easily disengaging the pad 128 from a patient's body (not shown). Accordingly, as shown connected in FIG. 3a, the pulse oximeter is configured to attach to a patient's body and emit light from one or more LEDs 119 through passages 124, 132 and 138 which is reflected, at least in part, from the patient's body and received by the photodetector 117, which in turn communicates data/information to the processing module 110 based on the reflected light. In one exemplary embodiment two LEDs 119 are provided wherein one is configured to emit light in the red wavelength range and the other is configured to emit light in the near-infrared wavelength range. Because deoxyhemoglobin has a higher optical extinction in the red region, and lower optical extinction in the near-infrared region, as compared to the optical extinction of oxyhemoglobin, the ratio of the quantity of the light emitted by each respective LED and reflected by the body correlates to the oxygen saturation of the blood. Accordingly, the data storage means 109 can be configured to store program instructions that, when implemented by the processor 107, receive information from the photodetector 117 and calculate the ratio of light received by the photodetector 117 at two specific wavelengths such as a red wavelength (e.g. 660 nm as 0.8 mW maximum average) and a near-infrared wavelength (e.g. 910 nm at 1.2 mW maximum average).

Referring to FIG. 3b, a top perspective view of an exemplary embodiment of a pulse oximeter according to the present invention is shown as including a top housing portion 102, a main housing portion 114, a bottom housing portion 120, and a pad 128. 102 Accordingly, the top housing portion 102 can be attached to the main housing portion 114 such as by snapping, clipping, latching, and/or engagement with one or more flexible tabs thereby providing convenient access to sensor components including, for example, the power supply 106 which, in the case of a battery, for example, may require replacement. In the exemplary pulse oximeter shown in FIG. 3b, the network interface 105 further includes a USB interface accessible externally from the top housing portion 102.

In the exemplary embodiment shown in FIG. 3b, the bottom housing portion 120 and pad 128 each commonly include one or more curved interior portions 148. As the material comprising the housing portion 120 and/or the pad 128 can be flexible, as described above, the curved portions 148 act to compress the material of the housing portion 120 and/or the pad 128 at a substantially intermediate portion so as to retain the pad 128 when slidably engaged with the bottom housing portion 120. Accordingly, a press fit is provided that will retain the bottom housing portion 120 as removably attached to the pad 128 upon patient motion.

The exemplary pulse oximeter embodiment shown in FIG. 3b further includes a user interface device 150; e.g., a button which is configured to toggle the operational mode of the herein described apparatus. In this specific embodiment, the data storage means 109 of the processing module 110, as discussed above, further include program instructions that, when implemented by the processor 107, communicate data received from the sensor module 118 to the network interface 105 based upon a transmission mode selected from the group consisting of continuous, episodic, and threshold modes as selected by user interaction with the user interface device 150. User interface device 150 can be configured to activate the device as well as set a default transmission mode such as a continuous transmission mode. A series of LEDs 140, 142, 144 are provided according to this specific version on the top housing portion 102102 for indicating to the user the specific transmission mode; for example, the continuous transmission mode is indicated to the illumination of LED 140. More specifically and in the continuous mode, data received by the photodetector 117 will be communicated to the network interface 105 at substantially real-time and without significant time delay or interval. In one exemplary embodiment, subsequent interaction with the user interface device 150 toggles the transmission mode of the herein described apparatus to an alternative episodic mode, thereby causing illumination of LED 142. In the episodic transmission mode, data received by the photodetector 117 is communicated to the network interface 105 at a pre-defined time interval, as stored in the data storage means 109. In this exemplary embodiment, though other permutations of the transmission mode order are contemplated, subsequent interaction with the user interface device 150 toggles the transmission mode of the apparatus to another alternative threshold transmission mode, thereby causing illumination of LED 144. In the threshold transmission mode, data received by the photodetector 117 is communicated to the network interface 105 only if the data is outside a pre-defined threshold value and/or range as stored in the data storage means 109. The episodic timer interval and/or threshold values can be stored in the data storage means 109 by the manufacturer or can be communicated to the data storage means 109 through care provider communication with the network interface 105. In an alternative embodiment, the transmission mode of the pulse oximeter apparatus can be indicated by an audible signal generated subsequent to user interaction with user interface device 150 as opposed to, or in combination with, a visually detectable illumination of one or more of LEDs 140, 142, 144. Still further, a fewer number of LEDs could be used for example, a single LED which is caused to intermittently blink or otherwise pulse according to a specific periodicity to indicate the transmission mode. In yet another embodiment, a second interface device (not shown) is provided to turn the apparatus on and off while the other interface device 150 is provided to toggle the transmission mode.

Accordingly and in terms of operation, a care provider, for example, places the pulse oximeter on a flat portion of a patient's chest (not shown), for example, by affixing the adhesive strip 136 attached to the pad 128. The adhesive strip 136 is attached to the pad 128 so as to substantially align passages 138 and 132 with one another. Next, the care provider engages the bottom housing portion 120, as previously attached to the main housing portion 114 and top housing portion 102, and the pad 128, such as by sliding the groove portions of bottom housing portion 120 into the tongues 130 of the pad 128 so as to substantially align the passages 124, 132, and 138 and retain the bottom housing portion 120 removably engaged with the pad 128. Next, the care provider engages the power button 108. In the embodiment shown in FIG. 1, the power button 108 is configured to communicate with the processing module 110 so as to engage the LEDs 119 and the photodetector 117. In the embodiment shown in FIG. 3b, the initial engagement with the power button 150 enables a continuous transfer mode as indicated by LED 140 with subsequent engagement with the power button 150 configured to toggle the transmission mode to episodic and threshold mode as indicated by LEDs 142 and 144, respectively. Upon engagement of the LEDs 119 and the photodetector 117, the photodetector 117 is configured to communicate data/information to the processing module 110 based on the light reflected from the patient's body. The processing module 110 is configured to interpret the data so as to calculate an oxygen saturation of the blood, for example. The data/information can be stored in data storage means 109 or the data/information and/or calculated value(s) can be immediately communicated to the network interface 105 depending on the selected transfer mode. The pulse oximeter can then be turned off when data retrieval has ended by subsequent user interaction (a second interaction with interface device 108 in the embodiment shown in FIG. 1 or a fourth interaction with interface device 150 in the embodiment shown in FIGS. 3a and 3b, for example) with the interface device 108. When the patient no longer requires monitoring, or in order to replace a sensor for various reasons, as the bottom housing portion 120 has not engaged the patient's body, it is slidably disengaged from the disposable pad 128 and the sensor can be reused. The pad 128 is then disengaged from the patient's body, such as by interaction with tab 133, and disposed.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A pulse oximeter, comprising:
   a reusable portion comprising:
      a housing having a first portion and a second portion, at least the second portion including a passage and made from a flexible material;
      a sensor module disposed within said housing, said sensor module including at least one light emitting diode and at least one photodetector;
      a processing module disposed within the housing and configured to communicate with the sensor module, the processing module including at least one processor, at least one network interface, and a power supply; and
   a disposable portion mountable to a patient, said disposable portion comprising:
      a disposable pad made from a flexible material and having at least a bottom surface and a passage; and
      an adhesive strip disposed on at least a portion of the bottom surface of the disposable pad wherein a feature on an outer periphery of the second portion of the housing is configured to releasably engage a feature on an outer periphery of the disposable pad to provide connectivity between the reusable portion and the disposable portion and such that the housing passage and the disposable pad passage are substantially aligned with one another.

2. The pulse oximeter of claim 1 wherein:
   the housing passage and the disposable pad passage are each configured to permit substantially unobstructed passage of light emitted from the at least one light emitting diode of the sensor module; and
   wherein at least one of the housing passage and the disposable pad passage is selected from the group consisting of an open aperture and a section of substantially transparent thermoplastic.

3. The pulse oximeter of claim 1 wherein the housing includes a top housing portion, a main housing portion and a bottom housing portion in which the top and main housing portions constitute the first portion and the bottom portion constitutes the second portion.

4. The pulse oximeter of claim 3 wherein the top portion of the housing is further configured to latchingly engage the main portion of the housing.

5. The pulse oximeter of claim 1 wherein the housing and the disposable pad are comprised of at least one material selected from the group consisting of thermoplastic polyurethane elastomer, polypropylene, pellethane, and polycarbonate resin thermoplastic material.

6. The pulse oximeter of claim 1 further including a power switch configured to communicate with the power supply and wherein the at least one light emitting diode is configured to be visible externally from the housing.

7. The pulse oximeter of claim 1 further including at least one printed circuit board disposed within the housing and further configured to mount the processing module.

8. The pulse oximeter of claim 1 wherein the feature on an outer periphery of the second portion of the housing includes at least one outer peripheral groove and wherein the feature on an outer periphery of the disposable pad includes at least one tongue disposed on the outer periphery thereof and wherein the housing is configured to releasably engage the disposable portion by slidable engagement of the at least one outer peripheral groove of the disposable pad with the at least one tongue of the second portion of the housing to enable the disposable portion to be releasably mounted to the remainder of the pulse oximeter.

9. The pulse oximeter of claim 1 wherein the adhesive applied to the disposable pad is an adhesive strip including a medical grade adhesive, the adhesive strip having at least one passage configured to be substantially aligned with the passage of the disposable pad when the strip is disposed on the disposable pad.

10. The pulse oximeter of claim 1 wherein the sensor module is disposed within the housing and proximate the housing passage.

11. The pulse oximeter of claim 1 wherein the network interface is configured to communicate data received from the sensor module by a protocol selected from the group consisting of at least one of USB, Wi-Fi, Bluetooth, IrDA, radio frequency, IEEE 802.11, IEEE 802.15 and Zigbee.

12. The pulse oximeter of claim 1 wherein the disposable pad is configured to be disposed proximate a user's body and the at least one photodetector is further configured to communicate data based on light emitted by the at least one light emitting diode and reflected from the user's body.

13. The pulse oximeter of claim 1 wherein the processing module further includes data storage means configured to store information received from the sensor module.

14. The pulse oximeter of claim 1 further including a user interface device, the processing module further including data storage means configured to store program instructions that, when implemented by the processor, communicates information received from the sensor module to the network interface based on a transmission mode including at least one of continuous, episodic, and threshold modes, the transmission mode being selectable based on user interaction with the user interface device.

15. The pulse oximeter of claim 1, in which a portion of the outer periphery of the second housing portion and the disposable pad are each inwardly curved to additionally provide retention between the pad and the housing.

16. A pulse oximeter, comprising:
a reusable portion that comprises:
a housing including at least a first portion and a second portion, the second portion being made from a flexible material and including at least one outer peripheral groove;
a sensor module including at least one light emitting diode and at least one photodetector; and
a processing module disposed within the housing, the processing module including at least a processor configured to communicate with the sensor module, a network interface, and a power supply; and
a disposable portion that comprises:
a disposable pad made from a flexible material and configured to be disposed proximate a target body and including at least one tongue disposed on an outer periphery; and
an adhesive disposed on at least a portion of the disposable pad, wherein the at least one outer peripheral groove of the second portion of the housing is configured to releasably and slidingly engage the at least one tongue of the disposable pad to provide releasable connectivity between the reusable portion and the disposable portion and such that the at least one light emitting diode and at least one photodetector have substantially unobstructed access to the target body.

17. A method of configuring an apparatus to permit measurement of oxygen saturation of blood, the method comprising the steps of:
providing a sensor module including at least one light emitting diode and at least one photodetector;
configuring a processing module to communicate with the sensor module, the processing module including at least one processor, at least one network interface, and at least one power supply, wherein each module is configured to be disposed within at least one portion of a housing, the housing including a first portion and a second portion in which the second portion is made from a flexible material;
removably adhering a disposable pad on a body of a patient, the disposable pad being made from an elastomeric material;
following said adhering step, engaging the housing and the disposable pad by engaging a feature on the outer periphery of the flexible second portion of the housing with a feature on the outer periphery of the flexible disposable pad;
illuminating at least a portion of the body with the at least one light emitting diode;
receiving light in the photodetector as reflected from the body; and
communicating data based on the reflected light to the processing module.

18. The method of claim 17 wherein the feature on an outer periphery of the flexible second housing portion includes at least one outer peripheral groove and the feature on an outer periphery of the disposable pad includes at least one tongue on the outer periphery thereof and wherein the engaging step includes the step of slidably engaging the outer peripheral groove of the housing and the tongue of the disposable pad.

19. The method of claim 17 further including the step of transmitting the communicated data by the network interface wherein the network interface is configured to communicate based on a protocol selected from the group consisting of USB, Bluetooth, IrDA, radio frequency, IEEE 802.11, IEEE 802.15 and Zigbee.

* * * * *